US008017110B1

(12) United States Patent
Goodrich et al.

(10) Patent No.: US 8,017,110 B1
(45) Date of Patent: Sep. 13, 2011

(54) INDUCTION OF AND MAINTENANCE OF NUCLEIC ACID DAMAGE IN PATHOGENS USING RIBOFLAVIN AND LIGHT

(75) Inventors: Raymond P. Goodrich, Lakewood, CO (US); Shawn D. Keil, Wheatridge, CO (US); Robert Owen Lockerbie, Littleton, CO (US); Vijay Kumar, Gold River, CA (US)

(73) Assignee: CaridianBCT Biotechnologies, LLC, Lakewood, CO (US)

( * ) Notice: Subject to any disclaimer, the term of this patent is extended or adjusted under 35 U.S.C. 154(b) by 0 days.

(21) Appl. No.: 13/155,983

(22) Filed: Jun. 8, 2011

Related U.S. Application Data

(63) Continuation of application No. 11/932,629, filed on Oct. 31, 2007, now Pat. No. 7,985,588, which is a continuation-in-part of application No. 10/648,536, filed on Aug. 25, 2003, now Pat. No. 7,901,673, which is a continuation of application No. 10/377,524, filed on Feb. 28, 2003, which is a continuation of application No. 09/586,147, filed on Jun. 2, 2000, now abandoned.

(60) Provisional application No. 60/319,488, filed on Aug. 23, 2002, provisional application No. 60/319,641, filed on Oct. 22, 2002.

(51) Int. Cl.
*A01N 63/00* (2006.01)
*A01N 1/02* (2006.01)
*C12N 13/00* (2006.01)
*C12N 5/07* (2010.01)
*C12N 5/10* (2006.01)
*C12N 5/071* (2010.01)
*C12N 5/00* (2006.01)
*C12N 5/02* (2006.01)

(52) U.S. Cl. .................... 424/93.1; 424/93.4; 424/93.6; 424/93.71; 435/2; 435/173.1; 435/363; 435/366; 435/372.2; 435/372.3; 435/325

(58) Field of Classification Search .................... None
See application file for complete search history.

(56) References Cited

OTHER PUBLICATIONS

Truitt et al. (J. Immunology, 163 (9): 5145-5156 (1999)).*

* cited by examiner

*Primary Examiner* — David J Steadman
*Assistant Examiner* — Jae W Lee
(74) *Attorney, Agent, or Firm* — Laura Butterfield Arciniegas; Edna M. O'Connor; John R. Merkling

(57) ABSTRACT

A process for damaging and maintaining damage to the nucleic acids of pathogens such as white blood cells, bacteria and viruses which may be contained in blood or blood components. This process comprises adding to the blood or blood component containing pathogens an effective amount of riboflavin, and exposing the fluid to light of an appropriate wavelength to damage the nucleic acid of the pathogen and to substantially maintain the damage to the pathogenic nucleic acids to allow for subsequent transfusion into a recipient.

5 Claims, 13 Drawing Sheets

Flow TACS DNA Fragmentation Assay with PET treated Human Jurkat T Cells

| treatment | Day 1 | | Day 2 | |
|---|---|---|---|---|
| | # of cells | % positive | # of cells | % positive |
| Saline/UV (7J/cm$^2$) | 345 | 85.5 | 3780 | 0.4 |
| Rf/UV (5J/cm$^2$) | 465 | 36.1 | 1425 | 87.5 |
| Saline/Vis (60 min) | 630 | 1.2 | 2865 | 1.6 |
| Rf/Vis (20 min) | 1020 | 44.6 | 10000 | 40.6 |

FIG. 4

TABLE 2. The production of cytokines by untreated or Mirasol-treated MNCs in response to LPS stimulation

| Cytokine | Untreated cells (pg/mL) | | Mirasol-treated cells (pg/mL) | |
|---|---|---|---|---|
| | With LPS | Without LPS | With LPS | Without LPS |
| IL-1β | 4357 ± 668 | 404 ± 301 | 14 ± 4* | 11 ± 2 |
| IL-2 | 4 ± 1 | 10 ± 4 | 1 ± 1* | 2 ± 1* |
| IL-4 | 10 ± 6 | 4 ± 2 | 2 ± 1 | 3 ± 1 |
| IL-5 | 2 ± 1 | 5 ± 6 | 1 ± 1 | 1 ± 1 |
| IL-6 | >5000 | >5000 | 8 ± 10* | 2 ± 1* |
| IL-8 | >5000 | >5000 | 1162 ± 425* | 1022 ± 286* |
| IL-10 | 1312 ± 117 | 128 ± 73 | 1 ± 1* | 1 ± 1* |
| IL-12p70 | 5 ± 4 | 4 ± 1 | 4 ± 2 | 2 ± 2 |
| TNF-α | 1274 ± 1328 | 67 ± 80 | 65 ± 45 | 61 ± 80 |
| IFN-γ | 2293 ± 2479 | 103 ± 117 | 4 ± 1 | 5 ± 1 |

\* Levels of cytokines present in the supernatants of Mirasol-treated cells are significantly less ($p < 0.05$) than the levels of cytokines present in the corresponding supernatants of untreated cells.

FIG. 12

TABLE 3. The production of cytokines by untreated or Mirasol-treated MNCs in response to anti-CD3 or anti-CD3+ anti-CD28

| Cytokine | Untreated cells (pg/mL) | | | Mirasol-treated cells (pg/mL) | | |
|---|---|---|---|---|---|---|
| | Anti-CD3 | Anti-CD3/28 | Medium | Anti-CD3 | Anti-CD3/28 | Medium |
| IL-2 | 8 ± 9 | 337 ± 559 | 5 ± 2 | 0 | 1 ± 1 | 1 ± 1* |
| IL-4 | 912 ± 549 | 1223 ± 596 | 1226 ± 1473 | 0* | 2 ± 1* | 1 ± 1 |
| IL-6 | >5000 | >5000 | >5000 | 0* | 2 ± 2* | 1 ± 1* |
| IL-10 | 205 ± 211 | 646 ± 247 | 355 ± 591 | 1 ± 1 | 1 ± 2* | 1 ± 2 |
| TNF-α | 1830 ± 354 | 4016 ± 470 | 96 ± 28 | 2 ± 1* | 1 ± 1* | 1 ± 1* |
| IFN-γ | >5000 | >5000 | 604 ± 103 | 0* | 3 ± 2* | 3 ± 2* |

\* Levels of cytokines present in the supernatants of Mirasol-treated cells are significantly less ($p < 0.05$) than the levels of cytokines present in the corresponding supernatants of untreated cells.

FIG. 13

INDUCTION OF AND MAINTENANCE OF NUCLEIC ACID DAMAGE IN PATHOGENS USING RIBOFLAVIN AND LIGHT

PRIORITY CLAIM

This application is a continuation of U.S. application Ser. No. 11/932,629 filed on Oct. 31, 2007, now allowed, which is a continuation-in-part of U.S. application Ser. No. 10/648,536 filed Aug. 25, 2003, now U.S. Pat. No. 7,901,673, which is a non-provisional of U.S. Provisional Application No. 60/319,488 filed Aug. 23, 2002, now expired; a non-provisional of U.S. Provisional Application No. 60/319,641 filed Oct. 22, 2002, now expired; and a continuation of U.S. application Ser. No. 10/377,524 filed Feb. 28, 2003, now pending, which is a continuation of U.S. application Ser. No. 09/586,147 filed Jun. 2, 2000, now abandoned.

BACKGROUND

Whole blood collected from volunteer donors for transfusion into recipients is typically separated into its components: red blood cells, white blood cells, platelets, plasma and plasma proteins, by apheresis or other known methods. Each of these blood components are typically stored individually and are used to treat a multiplicity of specific conditions and disease states. For example, the red blood cell component is used to treat anemia, the concentrated platelet component is used to control bleeding, and the plasma component is used frequently as a source of Clotting Factor VIII for the treatment of hemophilia.

After the components are separated, the white blood cell component is typically discarded, unless the cells are needed for specific applications such as photoimmune therapy or photophoresis. Cell separation procedures are not 100% effective. There is unusually some small percentage of other types of cells which are carried over into a separated blood component. Undesirable cells are typically cells of a different type which are carried over in some percentage into a desirable component. Cells such as white blood cells, which may transmit infections including HIV and CMV as well as causing other transfusion-related complications such as Transfusion-Associated Graft vs. Host Disease (TAGVHD), graft-vs-tumor responses and cytokine production are considered undesirable. The white blood cells present in the transfused blood product can also induce recipient immune responses directly by acting as antigen-presenting cells or indirectly by serving as a source of antigen that can be processed and presented by antigen-presenting cells. The recipient antidonor responses can include responses that eliminate donor cells, production of alloantiantibodies, and the induction of immunoregulatory responses that can result in increased infections, increased risk of tumor relapse, and enhanced survival of transplanted organs.

Ways to reduce the risks of these transfusion related complications from white blood cells is either to reduce the number of white blood cells transfused into a recipient, and/or to effectively destroy the viability and capacity of any transfused white blood cells to function post transfusion. White blood cells include granulocytes, monocytes and lymphocytes.

Current methods used to deplete contaminating white blood cells in blood products to be transfused include leukocyte filtration, UV irradiation of platelet concentrates and gamma irradiation of red blood cells and platelet concentrates. These methods do not completely eliminate the white blood cells however, and gamma and UV irradiation affect the cell quality of desired blood components such as platelets and red blood cells.

The blood or blood component to be transfused may also be contaminated with microorgansisms which may cause infections or unwanted immune reactions in the transfusion recipient. Microorganisms which may be present include, but are not limited to, viruses, (both extracellular and intracellular), bacteria, fungi, blood-transmitted parasites and protozoa.

Photosensitizers, or compounds which absorb light of a defined wavelength and transfer the absorbed energy to an electron acceptor may be a solution to the above problems, by inactivating pathogens contaminating a blood product without damaging the desirable components of blood. For the purposes of this invention, the general term "pathogen" may encompass any undesirable organism which may be found in blood or a blood product. Pathogens may be undesirable cells such as white blood cells, or may include microorganisms such as bacteria, parasites or viruses.

There are many pathogen reduction compounds known in the art to be useful for inactivating microorganisms or other infectious particles. Examples of such photosensitizers include porphyrins, psoralens, dyes such as neutral red, methylene blue, acridine, toluidines, flavine (acriflavine hydrochloride) and phenothiazine derivatives, coumarins, quinolones, quinones, and anthroquinones.

Dardare et al. showed in a study of the binding affinities of several common photosensitizers that both psoralen and methylene blue substantially bind to nucleic acids, phospholipid membranes and proteins in typical pathogen eradication experiments.

Although many publications have shown that damage to nucleic acids can be caused by photosensitizers and light, the issue of whether induction of damage to the nucleic acids of pathogens and undesirable cells is maintained over time, and after the pathogen reduced cells have been infused into a recipient has not been addressed.

One study done by R. Mababagloob et al. looked to see what effect S-59 and S-303 (psoralens) had on the DNA repair mechanisms of *D. radiodurans*, a bacteria which has multiple genomic copies and redundant repair mechanisms. The authors found that the above treatment in combination with UVA light or change in pH, resulted in 1 S-303 adduct for every 114 genomic DNA base pairs and 1 S-59 adduct for every 58 genomic DNA base pairs. However, this study did not examine whether the damage to the DNA was maintained after treatment, or was repaired by the bacteria. (Mababangloob, R., Castro, G., Stassinopoulos, A.; Helinx Technology, Utilized in the Intercept Blood System, Effectively Inactivates *Deinoccus radiodurans*, a Bacterium with Highly Efficienty DNA Repair; Abstract presented at the 44th Annual Meeting of the American Society of Hematology, 2002).

It is towards the method of pathogen reducing blood and blood components by inducing permanent damage to the nucleic acids of pathogens that the present invention is directed. Permanent damage means that the inactivated pathogens are unable to re-activate upon storage or upon infusion into a patient.

SUMMARY

The present invention is directed towards a method of substantially inactivating pathogens such as white blood cells, and microorganisms such as bacteria and viruses which may be present in a fluid to be transfused into a recipient. The invention is for a process for substantially maintaining damage to pathogen nucleic acid caused by a photosensitizer and light in a fluid containing pathogens and blood components comprising the steps of adding to the fluid a photosensitizer comprising riboflavin; irradiating the fluid and photosensitizer with light at an appropriate wavelength to activate the riboflavin to cause damage to the nucleic acid of the pathogen; and substantially maintaining the damage to the pathogen nucleic acid during storage and/or after transfusion of the fluid into a recipient.

BRIEF DESCRIPTION OF THE DRAWINGS

FIG. 4 is a table showing fragmentation of Jurkat cell DNA over a two-day period following treatment with riboflavin and either UV or visible light.

FIG. 6b is a graph which quantifies the percentage of intact (not fragmented) DNA from the gel shown in 6a.

FIG. 12 is a table showing the production of cytokines by treated or untreated MNCs in response to LPS stimulation.

FIG. 13 is a table showing the production of cytokines by treated or untreated MNCs in response to anti-CD3 or anti-CD3 and anti-CD28 stimulation.

DETAILED DESCRIPTION OF THE INVENTION

Figure 1:
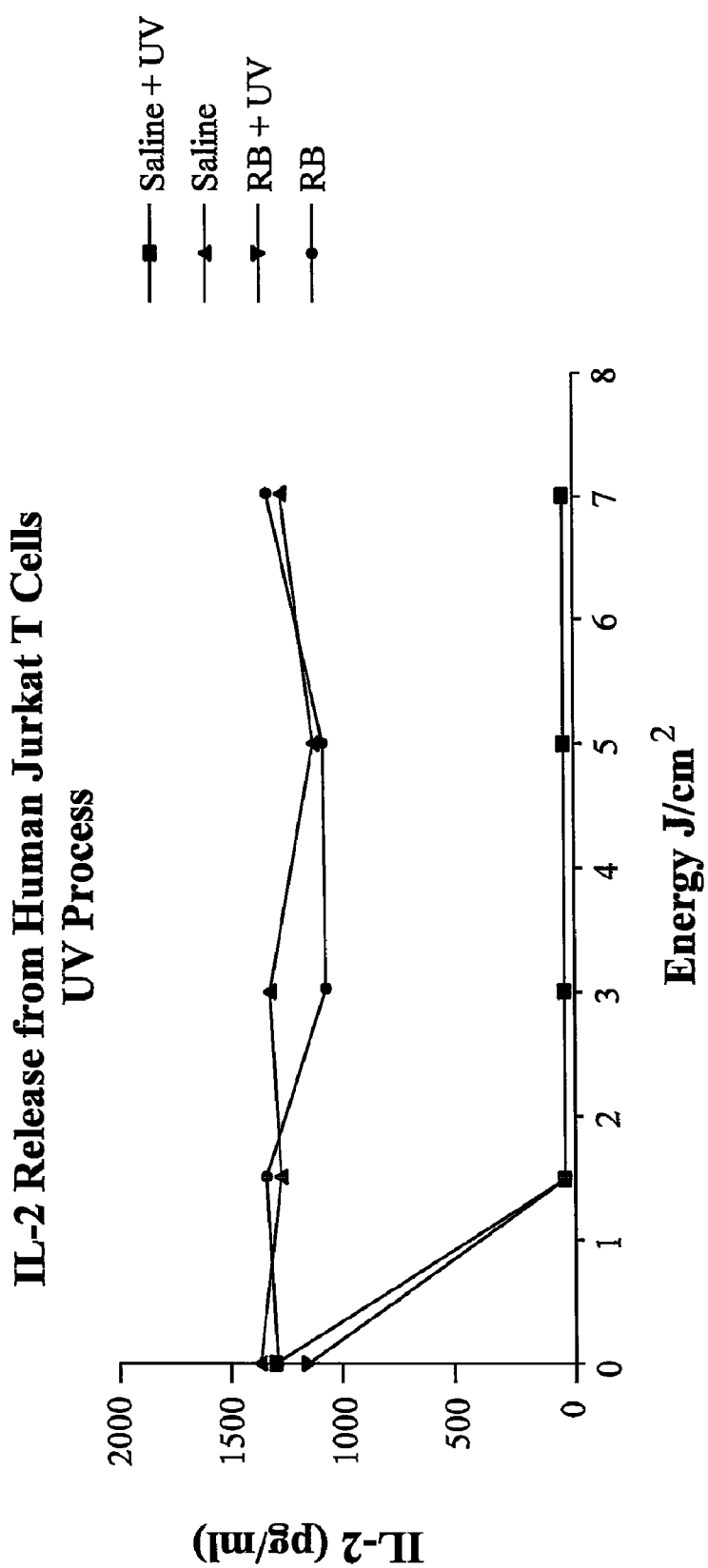
FIG. 1 is a graph showing the production of IL-2 from Jurkat cells after treatment with riboflavin and UV light.

A "photosensitizer" useful in this invention is defined as any compound which absorbs radiation at one or more defined wavelengths and subsequently utilizes the absorbed energy to carry out a chemical process. In this case, the desired photosensitizer will bind to any nucleic acids which are present in the fluid to be decontaminated to which the photosensitizer has been added. The chemical processes which occur damage any nucleic acids which may be in the fluid. The fluid may contain blood or blood products, or may be a solvent which requires sterility.

Endogenous photosensitizers are preferred for use in this invention. The term "endogenous" means naturally found in a human or mammalian body, either as a result of synthesis by the body or because of ingestion as an essential foodstuff (e.g. vitamins) or formation of metabolites and/or byproducts in vivo. When endogenous photosensitizers are used, particularly when such photosensitizers are not inherently toxic or do not yield toxic photoproducts after photoradiation, no removal or purification step is required after decontamination, and the decontaminated product can be directly returned to a patient's body or administered to a patient in need of its therapeutic effect.

Examples of such endogenous photosensitizers which may be used in this invention are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]) and alloxazine mononucleotide (also known as flavine mononucleotide [FMN] and riboflavine-5-phosphate). The term "alloxazine" includes isoalloxazines.

Use of endogenous isoalloxazines as a photosensitizer to pathogen reduce blood and blood components are described in U.S. Pat. Nos. 6,258,577 and 6,277,337 both issued to Goodrich et al., and are herein incorporated by reference to the amount not inconsistent.

Endogenously-based derivative photosensitizers include synthetically derived analogs and homologs of endogenous photosensitizers which may have or lack lower (1-5) alkyl or halogen substituents of the photosensitizers from which they are derived, and which preserve the function and substantial non-toxicity thereof. Such endogenously-based derivative photosensitizers which may be used in this invention are disclosed in U.S. Pat. No. 6,268,120 to Platz et al., which discloses alloxazine derivatives which may also be used to inactivate microorganisms contained in blood or blood components. This patent is incorporated by reference into the present invention to the amount not inconsistent herewith.

The photosensitizer compound riboflavin (7,8-dimethyl-10-ribityl isoalloxazine) has been reported to attack nucleic acids. Nucleic acids include both deoxyribonucleic acids and ribonucleic acids. Photoalteration of nucleic acid in the presence of riboflavin is discussed in Tsugita, A, et al. (1965), "Photosensitized inactivation of ribonucleic acids in the presence of riboflavin," Biochimica et Biophysica Acta 103:360-363; and Speck, W. T. et al. (1976), "Further Observations on the Photooxidation of DNA in the Presence of Riboflavin," Biochimica et Biophysica Acta 435:39-44. Binding of lumiflavin (7,8,10-trimethylisoalloxazine) to DNA is discussed in Kuratomi, K., et al. (1977), "Studies on the Interactions between DNA and Flavins," Biochimica et Biophysica Acta 476:207-217. Hoffmann, M. E., et al. (1979), DNA strand breaks upon exposure to proflavine and light are reported in Piette, J. et al. (1979), "Production of Breaks in Single- and Double-Stranded Forms of Bacteriophage ΦX 174 DNA by Proflavine and Light Treatment," Photochemistry and Photobiology 30:369-378, and alteration of guanine residues during proflavine-mediated photosensitization of DNA is discussed in Piette, J., et al. (1981), "Alteration of Guanine Residues during Proflavine Mediated Photosensitization of DNA," Photochemistry and Photobiology 33:325-333.

What has not been previously known or explored prior to the instant invention, is whether the strand breaks in the nucleic acids caused by the photolysis of riboflavin is permanent. That is, whether the nucleic acid repair mechanisms of the pathogen are unable to repair the damage caused by riboflavin and light and therefore prevent the pathogen from replicating. In this context, repair is defined as the molecular processes that are the basis for pathogen reactivation. Reactivation, or the synonymous term recovery, is defined as the regaining of, by a damaged pathogen, the capability to propagate and to form a colony.

Substantially maintaining the damage means that any damage sustained by the nucleic acids of pathogens is maintained over time so that when the blood product, which has been treated with riboflavin and light is transfused into a recipient, the inactivated pathogen will not self-repair the damaged nucleic acids, and reproduce in the transfusion recipient. Transfusion related complications caused by viable pathogens which may be contained in the pathogen reduced blood or blood product will therefore be substantially reduced.

The method of this invention requires mixing the photosensitizer with the whole blood or with the separated blood component to be decontaminated. Mixing may be done by simply adding the photosensitizer or a solution containing the photosensitizer to a fluid to be decontaminated. In one embodiment, the material to be decontaminated to which photosensitizer has been added is flowed past a photoradiation source, and the flow of the material generally provides sufficient turbulence to distribute the photosensitizer throughout the fluid to be decontaminated. In another embodiment, the fluid and photosensitizer are placed in a photopermeable container and irradiated in batch mode, preferably while agitating the container to fully distribute the photosensitizer and expose all the fluid to the radiation.

The amount of photosensitizer to be mixed with the fluid will be an amount sufficient to adequately inactivate any pathogenic nucleic acids which may be present in the fluid, but less than a toxic (to the desired components) or insoluble amount. If riboflavin is used as the photosensitizer, it may be added to the fluid at a final concentration of between about 50-500 μM. Pathogenic nucleic acid includes any undesirable nucleic acid such as nucleic acid from white blood cells, bacteria or viruses. Nucleic acids include either deoxyribonucleic acid (DNA), ribonucleic acid (RNA) or both.

The fluid containing the photosensitizer is exposed to light of the appropriate wavelength to activate the photosensitizer and to cause substantially permanent damage to the pathogenic nucleic acids. The pathogen reduced fluid may then be stored for a period of time before being transfused into a recipient, or may be transfused into a recipient directly after the pathogen reduction procedure.

Example 1

To determine the effectiveness of isoalloxazine (riboflavin) photosensitizer and light in damaging and maintaining the damage to nucleic acids of white blood cells that may be contained in a solution of red blood cells or platelets, Jurkat cells (a model T-lymphocytic cell line) were spiked into solutions containing either red blood cells or platelets. Jurkat cells were initially grown in RPMI cell growth medium at 37° C. in 5% $CO_2$.

Set forth below is one protocol which may be used in this invention for determining the effectiveness of riboflavin and light in causing damage to and subsequently maintaining the damage to the nucleic acids of any contaminating white blood cells in a solution containing red blood cells.

Fluid containing red blood cells and having 5% plasma carryover may be placed into any container known in the art. A 1 L bag is one such example, not meant to be limiting. A quencher may also be optionally added to the fluid. Such quenchers may include antioxidants or other agents to prevent damage to desired fluid components or to improve the rate of inactivation of microorganisms. Quenchers useful in this invention are exemplified by glutathione, n-acetyl-cysteine, cysteine, adenine, histidine, tyrosine, tryptophan, ascorbate, vitamin E, trolox, TPGS and mixtures thereof. Riboflavin was added to the cells at a final concentration of 500 μM either with the quencher (if optionally added) or separately. Any means known in the art for adding the photosensitizer to the fluid to be decontaminated and for placing the fluid in the container may be used. Such means typically include flow conduits, ports, reservoirs, valves, and the like. Additives which enhance blood component viability after treatment with riboflavin and light may also be added either pre or post illumination. Examples of additives which may be added to the fluid may include methylxanthines and/or PGE1.

Air was added to the fluid containing red blood cells and riboflavin at a volume of 133 mL for every 266 mL of fluid. Air may be added to the fluid contained in the bag by any means known in the art. The fluid containing red cells was then "spiked" with Jurkat cells at a concentration of $10^6$/mL to simulate white blood cell carryover in a collection procedure. The fluid containing red blood cells and spiked Jurkat cells was illuminated with light in the visible (from a source having a peak emission at 447 nm) spectrum at an intensity of 190 J/cm$^2$. Treated cells and untreated controls were incubated for 24 hours at 37° C. in growth medium to assess long term survival of cells which were not killed during the illumination process. After treatments, the Jurkat cells were recovered and assayed for cell viability markers, such as production of IL-2, cell proliferation and fragmentation of DNA.

A similar protocol was used to determine the effectiveness of inactivating white blood cells and maintaining the inactivation of the cells in a solution containing platelets. A final concentration of 50 μM isoalloxazine was added to platelets collected by apheresis with a 90% plasma carryover. The fluid containing platelets was "spiked" with Jurkat cells at a concentration of $10^6$/mL to simulate white blood cell contamination. The fluid containing platelets and spiked Jurkat cells was illuminated with light in the ultraviolet (UV) spectrum at 320 nm and an intensity of 7 J/cm$^2$. After treatments, the Jurkat cells were recovered and assayed for markers of cell viability, such as production of IL-2, cell proliferation and fragmentation of DNA.

Jurkat cell death was assessed with the Molecular Probes Live/Dead Cytotoxicity/Viability assay. Cells were exposed to a staining solution containing ethidium homodimer-1 which stains non-viable (dying or dead) cells orange/red and calcein AM which stains viable (live) cells green. Cells with holes in their membrane appear red/orange when stain is excited with 495 nm light. Intact cells stain green. Cells that appear orange and that contain no green are counted as dead cells; green cells that contain no orange stain are counted as live. Dead cells in a sample are expressed as a percentage of the total number of cells present in a sample.

Figure 2:
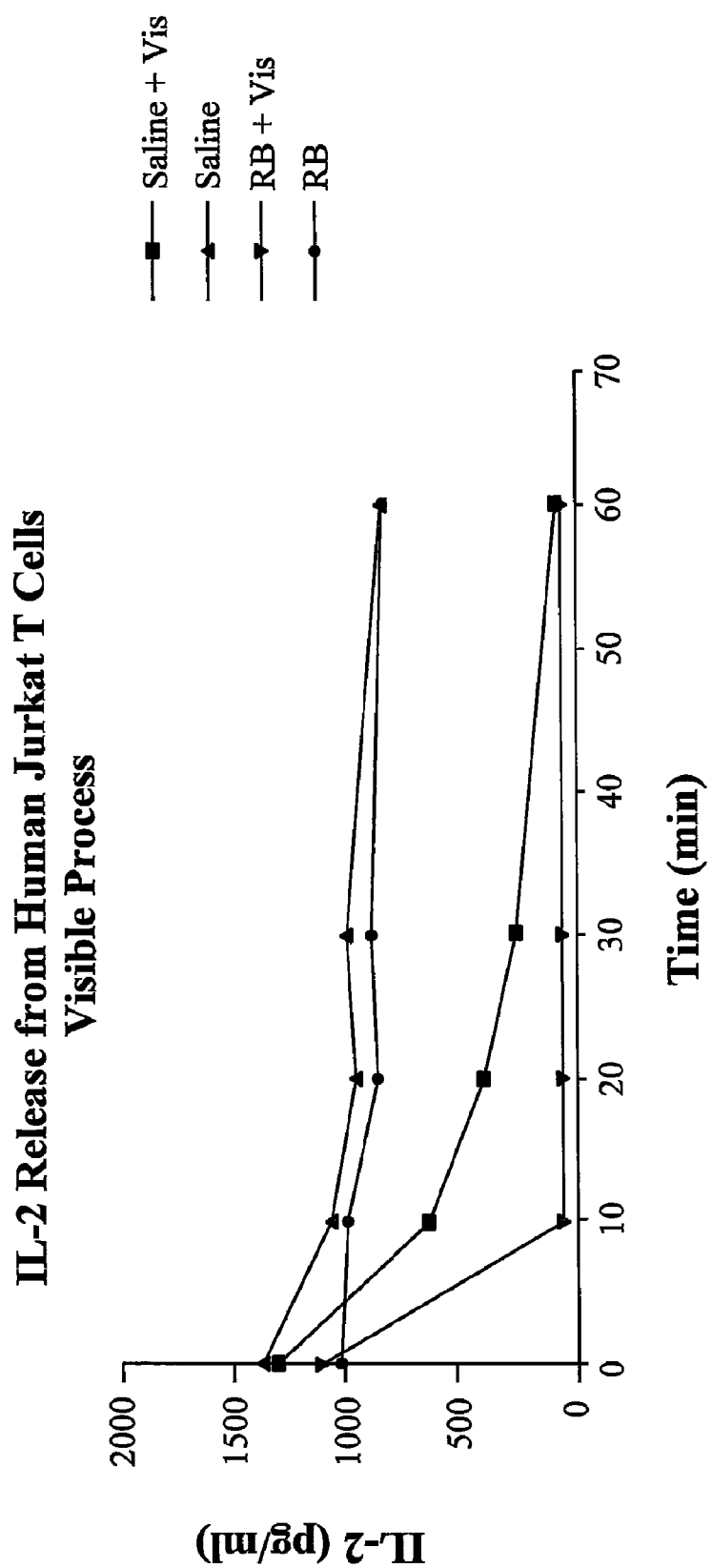
FIG. 2 is a graph showing the production of IL-2 from Jurkat cells after treatment with riboflavin and visible light.

FIGS. 1 and 2 show release of IL-2 over time by Jurkat cells after stimulation with PMA and PHA. Jurkat cells were treated with riboflavin (designated Rb in these Figs.) and either UV (ultraviolet) (see FIG. 1) or visible light (see FIG. 2) and then stimulated to produce IL-2. The addition of saline alone (no riboflavin, no light) or riboflavin alone (no light) serves as the experimental controls. Production of IL-2 by Jurkat cells upon stimulation with PMA and PHA is a measure of T-cell viability. After treating the cells with riboflavin and light, PMA and PHA are added to induce production of IL-2 and the cells are incubated overnight. IL-2 in the supernatent is detected using an ELISA assay.

FIG. 1 shows IL-2 release from Jurkat cells after exposure to riboflavin and UV light. Although difficult to see due to the substantially similar results, UV alone, as well as riboflavin in combination with UV light cause losses in cell viability and subsequent decrease in IL-2 release.

FIG. 2 shows IL-2 release from Jurkat cells after exposure to riboflavin and visible light. As can be seen from FIG. 2b, cells treated with riboflavin and visible light cause substantial losses in cell viability and subsequent decrease in IL-2 release. Visible light alone also causes a decrease in the amount of cell viability and subsequent release of IL-2, but not to the same extent as the combination of riboflavin and visible light.

Example 2

Figure 3A:
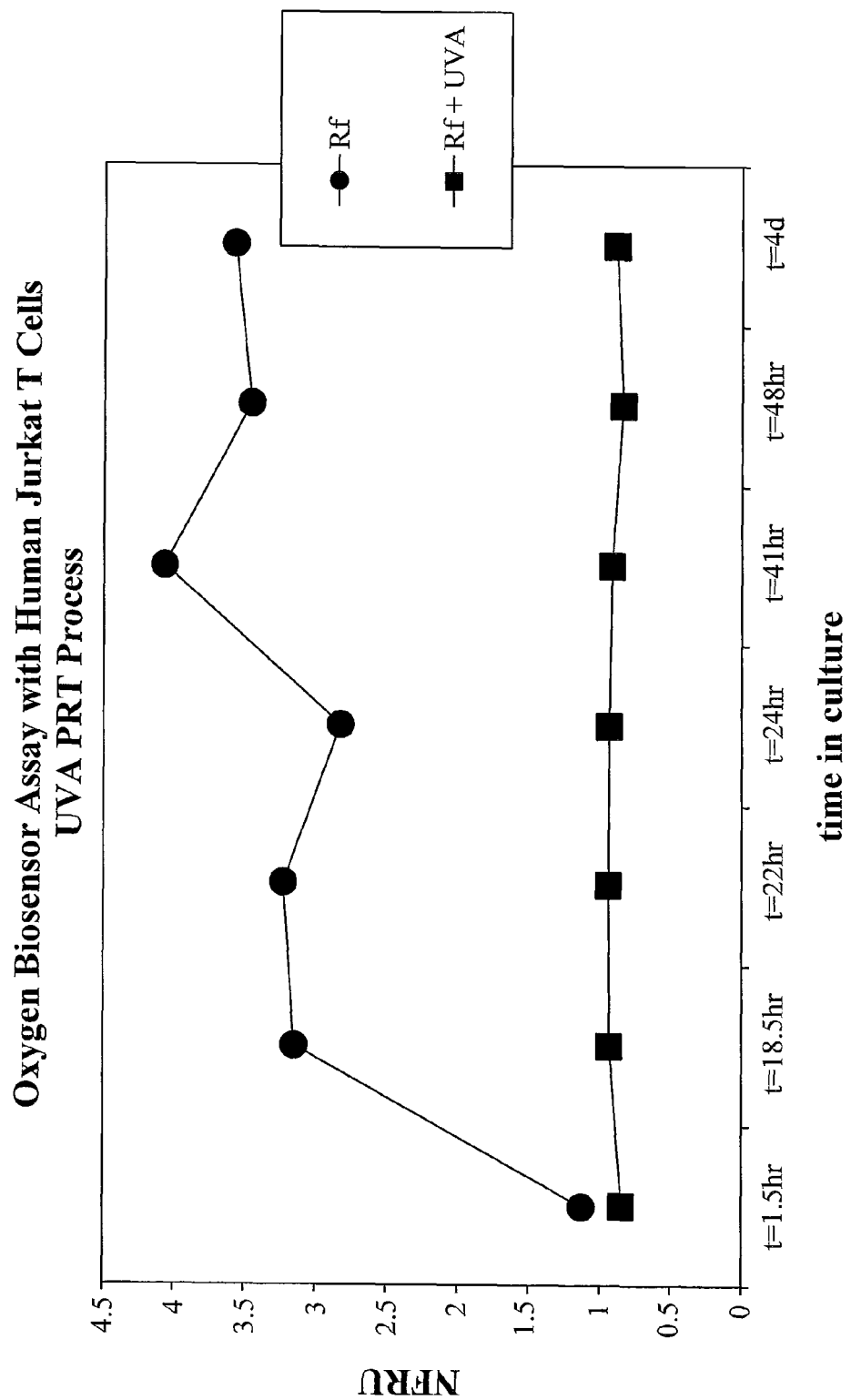
FIG. 3a is a graph showing oxygen consumption of Jurkat cells after treatment with riboflavin and UV light.
Figure 3B:
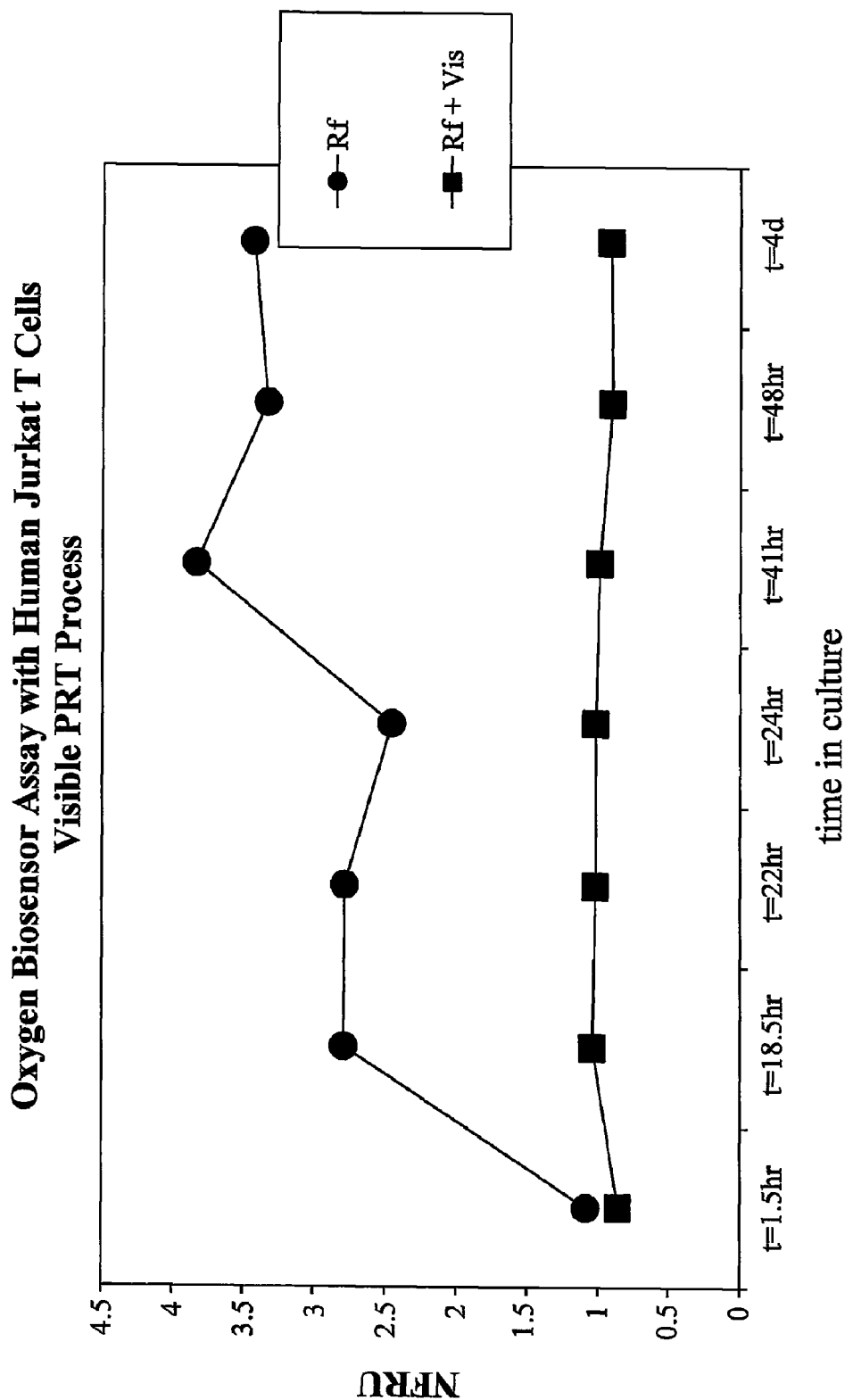
FIG. 3b is a graph showing oxygen consumption of Jurkat cells after treatment with riboflavin and visible light.

FIGS. 3a and 3b are graphs showing oxygen consumption of treated and control Jurkat cells. Oxygen consumption is a measure of cell viability. Healthy cells respire and consume oxygen, unhealthy and/or dead cells do not. A BD oxygen biosensor system was used to monitor Jurkat cell metabolism for a period of 4 days after treatment. Oxygen diffuses into the cell media from the atmosphere. The presence of oxygen quenches a fluorescent marker located at the bottom of the wells where the cells are grown. The amount of oxygen consumed by the cells is measured by the amount of fluorescence being produced. Where oxygen is used by healthy cells for respiration, fluorescence is produced.

FIG. 3a is a graph measuring the amount of fluorescence (NFRU) generated over time in Jurkat cells treated with riboflavin (designated Rf in these Figs.) and UV light. Cells which have been treated with riboflavin and UV light are damaged by the process. Consequently, the cells are not metabolically active and therefore consume no oxygen, thus producing little to no fluorescence.

FIG. 3b is a graph measuring fluoresce (NFRU) generated over time in Jurkat cells treated with riboflavin and visible light. Cells treated with riboflavin and visible light are damaged by the process. As shown in FIG. 3b, treated cells are not metabolically active and do not consume oxygen over a four day period. Little to no fluorescence is produced.

Example 3

FIG. 4 shows fragmentation of DNA of Jurkat cells over a two day period following treatment with riboflavin and either visible or ultraviolet light. Strand breaks in the DNA of Jurkat cells were measured by flow cytometry after treatment with riboflavin (designated Rf in this Fig.) and light. % positive signifies positive DNA damage. As seen in the table, on day one, UV light alone causes DNA damage in 85.5% of cells. On day 2 however, only 0.4% of the cells exposed to UV light alone displayed DNA damage. As shown in FIG. 4, exposure of the cells to UV light alone does not maintain DNA damage over time. One hypothesis is that the cells exposed to UV light alone may repair the damage. Another hypothesis is that UV alone may not prevent the growth of new healthy cells.

Upon treatment with riboflavin and UV light however, 36.1% of the DNA in the treated cells were damaged, while on day 2, 87.5% of the treated cells manifested DNA damage. The addition of riboflavin appears to maintain the damage to DNA caused by exposure to UV light.

Visible light alone did not cause DNA damage, however with the addition of riboflavin, FIG. 4 illustrates that DNA was damaged and the damage was substantially maintained over a two day period.

From the data presented above, the addition of riboflavin or other endogenous alloxazine derivatives appears to maintain the damage to white blood cell DNA.

From FIG. 4 it can be seen that the addition of riboflavin in combination with exposure to either visible or UV light not only causes fragmentation of Jurkat DNA, but maintains the damage over time.

Figure 5:
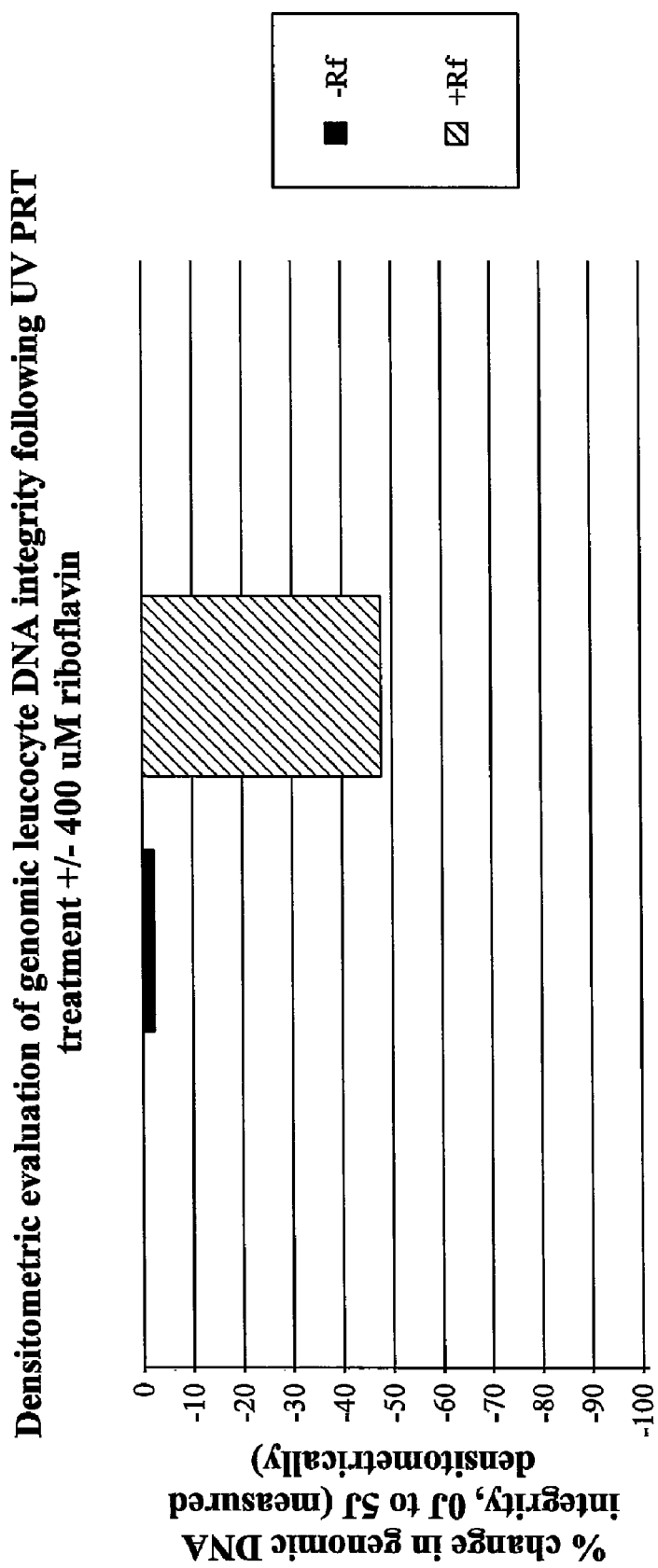
FIG. 5 is a graph measuring the percent change in the integrity of the genomic DNA of separated human leukocytes following treatment with ultraviolet light and with and without riboflavin.

FIG. 5 is a graph showing the percentage of DNA fragmentation of human leukocyte genomic DNA on an agarose gel. $3.8 \times 10^5$ autologous cells/mL in 90% plasma were added to a 1 L ELP bag. Riboflavin at a final concentration of 400 µM was added and the cells were irradiated at 320 nm at a total intensity of 5 J/cm$^2$. As can be seen from this graph, the DNA of autologous white blood cells showed around a 50% change in integrity after being exposed to riboflavin and light as compared to cells exposed to light alone. This result corresponds to the results obtained with Jurkat cells.

Example 4

To measure the effect of riboflavin and light on bacterial DNA kill, E. coli was spiked into 90% plasma. Riboflavin at a final concentration of 50 µM was added and the mixture was exposed to light at an intensity range of 0 J/cm$^2$, 10 J/cm$^2$, 17 J/cm$^2$ and 20 J/cm$^2$. After light exposure, the bacterial genomic DNA was purified using standard DNA purification techniques, and the DNA fragmentation was analyzed by standard agarose gel electrophoresis and fragmentation of the DNA was quantified using standard imaging techniques.

Figure 6A:
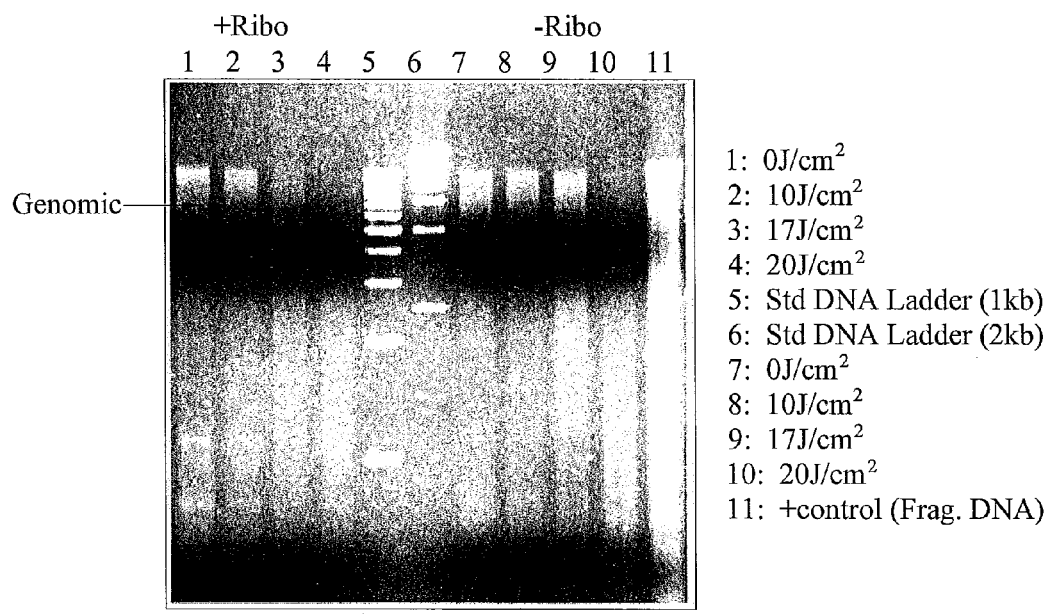
FIG. 6a is an agarose gel showing laddering of DNA after treatment with and without ultraviolet light and riboflavin.
Figure 6B:
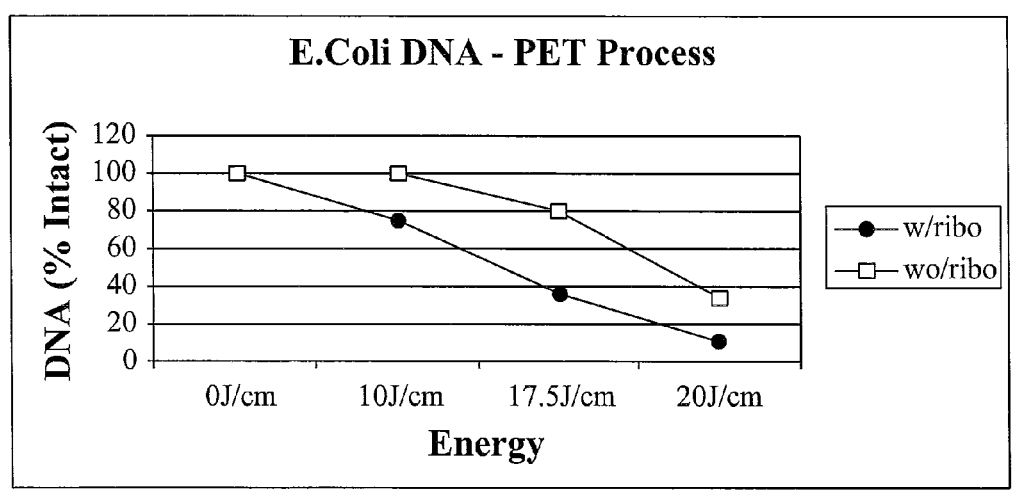

FIG. 6b is a graph showing the percentage of fragmentation of DNA (measured in terms of the percentage of DNA intact after treatment) of E. coli after exposure to UV light either with or without riboflavin. As can be seen in both the gel (see FIG. 6a) and the graph, (see FIG. 6b) the combination of riboflavin and UV light induced much greater bacterial DNA fragmentation than that induced by UV light alone. More DNA degradation occurs at lower energies with riboflavin than without.

Example 5

This study was done to determine if riboflavin and 320 nm broadband UVB light causes irreparable damage to the DNA of viruses.

It is known that UV light causes nucleic acid damage to cells. However, exposure to UV light also causes up regulation of cellular repair mechanisms. In the literature it has been reported that viruses inactivated with UV light alone will reactivate a small percentage of the time due to concurrent up regulation of the host cell's nucleic acid repair mechanisms.

To test if riboflavin and light has the same inactivating effect on the nucleic acid of viruses as it does on white blood cells and bacteria, E. coli was chosen as the host cell for lambda-phage virus. E. coli was irradiated with UV light to initially up regulate the host cells nucleic acid repair mechanisms. In this experiment, if the nucleic acid repair mechanisms of the host cell are up regulated upon initial exposure to UV light, any viral reactivation effect should be amplified. Any prevention of viral reactivation should be easily quantified.

After initial exposure to UV light, host E. coli was placed into Luria Broth growth media for 1-2 hours. Meanwhile, the lambda phage virus was irradiated with 320 nm UVB light at an intensity of 0.08 J/cm$^2$ in PBS and riboflavin at final concentrations of between 0-300 µM until a two log viral kill was achieved. The irradiated virus was then incubated with either irradiated or non-irradiated E. coli host cells for 20 minutes to allow for viral absorption. The virus infected E. coli samples were plated and allowed to grow overnight. At this time the plaques were counted to determine the number of infectious particles.

Figure 7:
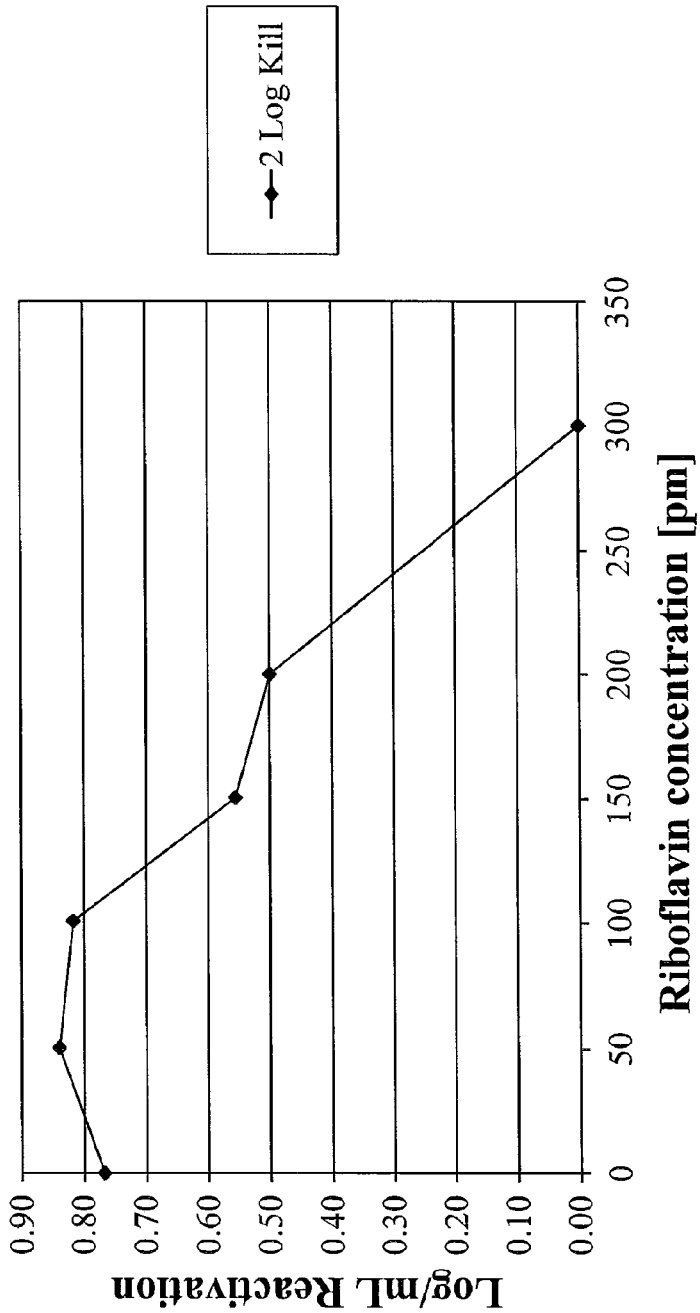
FIG. 7 shows the log reactivation of lambda-phage virus after treatment with riboflavin and ultraviolet light.

FIG. 7 shows the amount of log virus reactivation at increasing concentrations of riboflavin. The effect of riboflavin on preventing virus reactivation was dose dependant.

Approximately 0.8 log virus reactivation occurred over a concentration of 0-100 μM riboflavin. At riboflavin concentrations greater than 100 μM, reactivation was progressively prevented with no reactivation occurring at 300 μM.

These results suggest that irradiation of virus with both riboflavin and light prevents reactivation of viral DNA.

Example 6

The high incidence of mortality associated with TAGVHD eliminates the use of clinical trials to study the effectiveness of various treatments in preventing TAGVHD. This has led to a search for in vitro assays that would be representative of the in vivo responses that contribute to the development of TAGVHD. Some of the in vitro assays that may be used to measure this response include proliferation of MNCs in response to a number of stimuli including mitogens, allogeneic stimulator cells, or to T-cell antibodies; and the ability to stimulate proliferation of normal responder cells. These in vitro assays were used to test the effect of riboflavin and light on the function of human mononuclear white blood cells (MNCs).

Methods

The proliferative ability of MNCs in response to a number of different stimuli was studied. MNCs were obtained by discontinuous centrifugation with Ficol-Hypaque of WBCs obtained from the leukoreduction portion of a standard apheresis platelet collection on an automated blood collection machine. The MNCs were resuspended in autologous platelelet poor plasma and split into two 250 mL samples for a test sample and a control sample. The test samples were treated with 35 mL of a 500 μM riboflavin solution in 0.9% saline. All samples were then exposed to 6.2 J UV light per mL product for approximately 8 to 10 minutes. After treatment, the cells from both test and control samples were pelleted by centrifugation, washed and resuspended in RPMI 1640 containing 10% fetal calf serum for the assays described below.

The proliferative response of MNCs to bind anti-CD3 and anti CD28 antibodies was tested by adding 50 μL of PBS containing 10 μg per mL anti-CD3 or PBS containing 10 μg per mL anti CD3 plus 4 μg per mL anti CD28 or PBS alone to 96 well flat bottom plates. The plates were incubated for 90 minutes at room temperature, washed twice with PBS, and then 100 μL RPMI 1640 containing 5% human AB serum and penicillin-streptomycin was added to each well. After a 1 hour incubation at room temperature, 100 μL peripheral blood MNCs at $2 \times 10^6$ cells per mL were added to each well. The plates were incubated for 3 days and pulsed with [$^3$H] thymidine for 4 hours and harvested.

Cytokine levels were determined by measuring the supernatants from the wells of MNCs ($5 \times 10^6$ MNCs/mL RPMI 1640 containing 10% FCS) that had been cultured for 24 hours with or without 100 ng per mL lipoploysaccharide (LPS) or for 3 days with anti-CD3 or anti-CD3 and anti-CD28 coated plates (prepared as described above) or with medium alone. The levels of IL-1β, IL-6, IL-8, IL-10, IL-12p70, TNF-α, IL-2, IL-4, IL-5, IL-10, TNF and IFN-γ, were measured with the CBA human inflammatory cytokine kit (BD Biosciences, PharMingen).

Results

Figure 8:
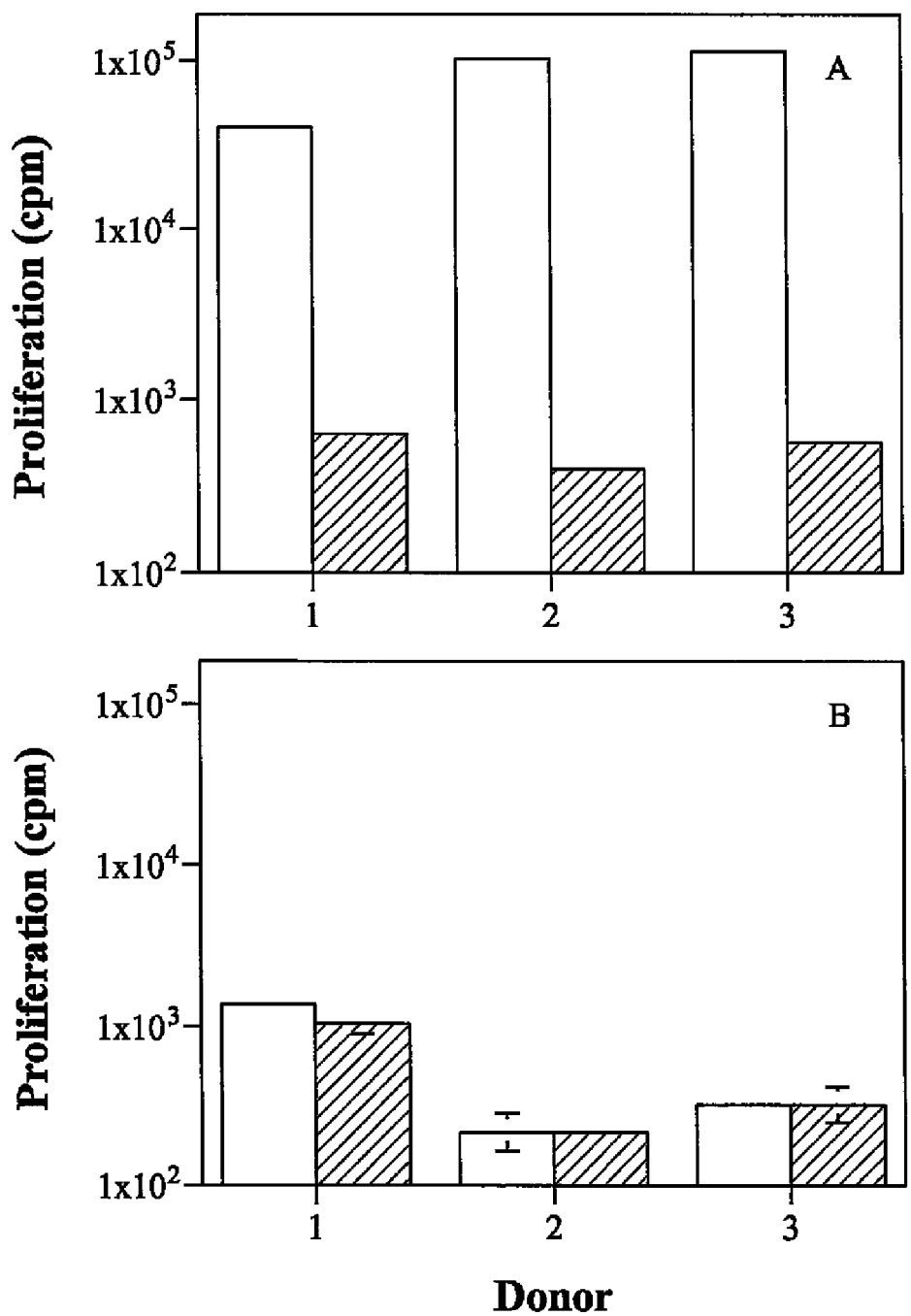
FIG. 8 is a graph showing the effect of riboflavin and light treatment on the proliferative response of human MNCs to mitogenic stimulation.

As seen in FIG. 8, the ability of MNCs treated with riboflavin and light to proliferate in response to mitogenic stimulation was tested by incubating riboflavin treated (see Graph B) or control untreated (see Graph A) human MNCs with the mitogen PHA. As seen in Graph B, treatment with riboflavin completely inhibited the ability of the MNCs to proliferate in response to mitogenic stimulation compared to the control treatment.

Figure 9:
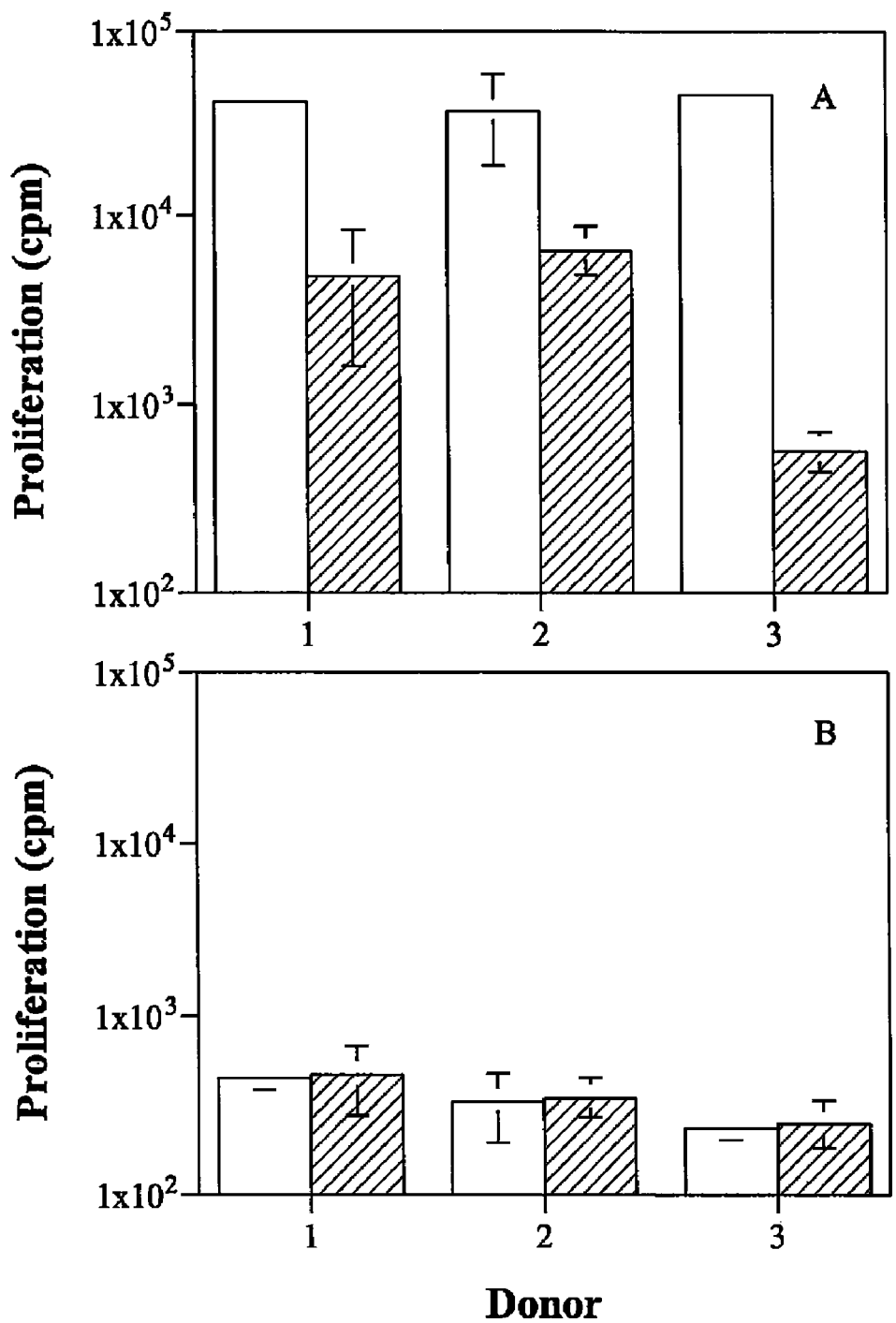
FIG. 9 is a graph showing the effect of riboflavin and light treatment on the proliferative response of human MNCs to allogenic stimulator cells.

The effect of riboflavin and light on the proliferative response of MNCs to allogeneic stimulator cells is shown in FIG. 9. As in FIG. 8 above, treatment with riboflavin and light completely inhibited the ability of MNCs to proliferate in response to stimulation by allogenic stimulator cells compared to the control treatment.

Figure 10:
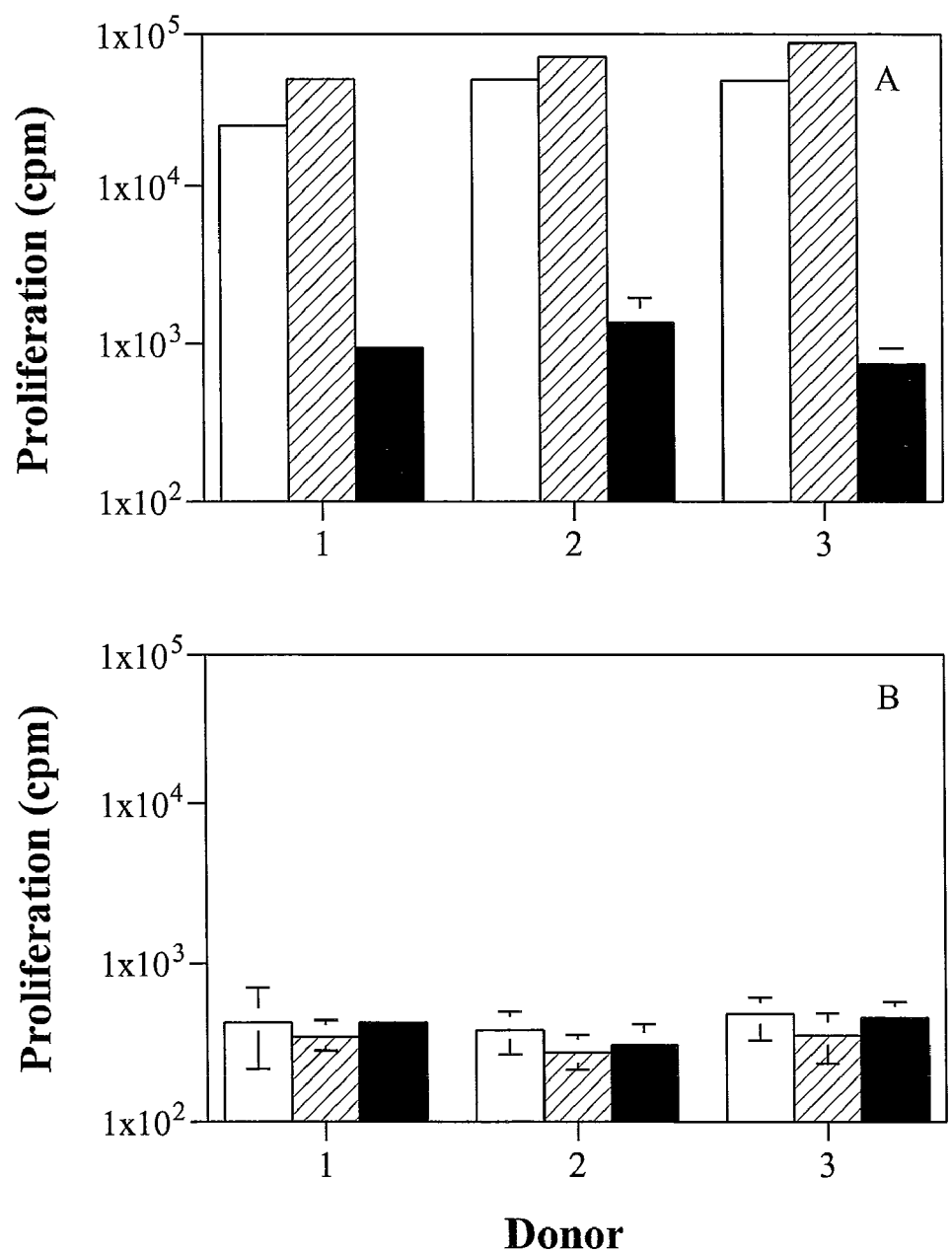
FIG. 10 is a graph showing the effect of riboflavin and light treatment on the proliferative response of human MNCs to anti-CD3 or anti-CD3 and anti-CD28 stimulation.

The effect of riboflavin and light on the proliferative response to anti-CD3 or anti-CD3 plus anti-CD28 is shown in FIG. 10. The results again demonstrate that no detectable MNC proliferation was induced by these stimuli in riboflavin-treated cells as compared to the control treatment.

Figure 11:
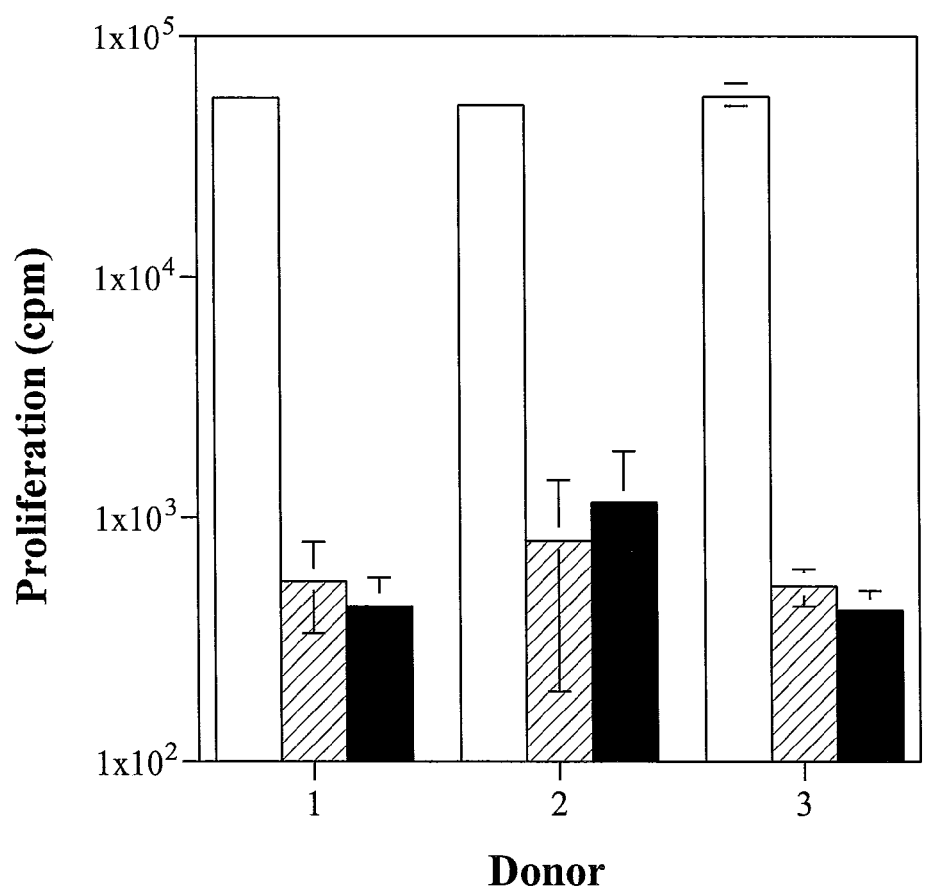
FIG. 11 is a graph showing the effect of riboflavin and light treatment on the ability of MNCs to stimulate the proliferation of allogeneic responder cells.

MNCs present in blood products are capable of presenting antigens to recipient cells and inducing a response by the recipient cells. As seen in FIG. 11, when riboflavin-treated MNCs were tested for their ability to induce proliferation of allogeneic responder cells, the riboflavin treated cells were unable to stimulate any proliferation by the allogeneic responder cells. This indicates that riboflavin and light are able to inhibit antigen presentation capabilities of the riboflavin and light-treated cells.

Another measure of the functionality of MNCs is to measure the cytokines that are produced in response to stimulation. Stimulation of MNCs with LPS produces cytokines as a result of signaling via myeloid cells, while stimulation of MNCs with anti-CD3 plus anti-CD28 produces cytokines as a result of signaling via T-cells.

As shown in FIG. 12, incubation of MNCs with LPS resulted in barely detectable levels of IL-2, IL-4, IL-5 and IL-12p70 in the supernatants of either treated or control cells. However, LPS did induce production of IL-1β, IL-10, IFN-γ, and TNF-α in control cells but not in treated cells.

As seen in FIG. 13, increased production of IL-2, IL-10, TNF-α and IFN-γ was seen when control MNCs were incubated with the T-cell mitogens anti-CD3 and anti-CD3 plus anti-CD28, but not in the treated cells.

The results of these assays show that treatment of human MNCs with riboflavin and light functionally inactivate MNCs, as well as inducing irreparable damage to the nucleic acids of the cells.

The invention claimed is:

1. A process for inhibiting self-repair of nucleic acid of pathogenic white blood cells, bacteria and/or viruses which may be contained in blood components comprising the steps of:

adding to the blood components riboflavin acting as a photosensitizer at a final concentration of between about 50-500 μM;

irradiating the blood components and riboflavin acting as a photosensitizer with light in a visible or UV range at an appropriate wavelength to activate the riboflavin acting as a photosensitizer to fragment the nucleic acid of the pathogenic white blood cells, bacteria and/or viruses to inhibit self-repair of the nucleic acid; and wherein the inhibition of nucleic acid self-repair caused by the photosensitizer and light is maintained over time such that the pathogenic white blood cells, bacteria and/or viruses will not reproduce in the blood components.

2. The process of claim 1 further comprising adding to the blood components and riboflavin acting as a photosensitizer a solution containing additives to enhance blood component viability.

3. The process of claim 1 wherein the blood component further comprises platelets.

4. The process of claim 1 wherein the blood component further comprises red blood cells.

5. The process of claim 1 wherein the light used to irradiate the blood components and riboflavin acting as a photosensitizer is in the UVB range.

* * * * *